(12) United States Patent
Bal et al.

(10) Patent No.: US 9,421,112 B2
(45) Date of Patent: Aug. 23, 2016

(54) FIXATION SYSTEM FOR SPINAL CAGES

(75) Inventors: Kamil Bal, Ankara (TR); Ibrahim Ozgur Bektas, Ankara (TR)

(73) Assignee: Tria Spine Meikal Ltd. Sti., Ankara (TR)

( * ) Notice: Subject to any disclaimer, the term of this patent is extended or adjusted under 35 U.S.C. 154(b) by 200 days.

(21) Appl. No.: 14/356,861

(22) PCT Filed: Jun. 14, 2012

(86) PCT No.: PCT/IB2012/053015
§ 371 (c)(1),
(2), (4) Date: May 7, 2014

(87) PCT Pub. No.: WO2013/008111
PCT Pub. Date: Jan. 17, 2013

(65) Prior Publication Data
US 2015/0100127 A1    Apr. 9, 2015

(30) Foreign Application Priority Data

Jul. 14, 2011 (TR) ................. a 2011 07005

(51) Int. Cl.
*A61F 2/44* (2006.01)
*A61F 2/30* (2006.01)

(52) U.S. Cl.
CPC .............. *A61F 2/447* (2013.01); *A61F 2/4455* (2013.01); *A61F 2002/3008* (2013.01); *A61F 2002/3052* (2013.01); *A61F 2002/30266* (2013.01); *A61F 2002/30331* (2013.01); *A61F 2002/30364* (2013.01); *A61F 2002/30472* (2013.01); *A61F 2002/30492* (2013.01); *A61F 2002/30507* (2013.01); *A61F 2002/30579* (2013.01);
(Continued)

(58) Field of Classification Search
CPC ...................................... A61F 2/447

USPC ............................ 623/17.11, 17.16
See application file for complete search history.

(56) References Cited

U.S. PATENT DOCUMENTS

| 6,102,949 A | 8/2000 | Biedermann et al. |
| 6,443,990 B1 * | 9/2002 | Aebi ..................... A61F 2/4455 606/247 |

(Continued)

FOREIGN PATENT DOCUMENTS

| FR | 2846876 A1 | 5/2004 |
| FR | 2880795 A1 | 7/2006 |

(Continued)

OTHER PUBLICATIONS

Machine translation of WO/2010/037926, accessed Dec. 14, 2015.*

*Primary Examiner* — Jan Christopher Merene
(74) *Attorney, Agent, or Firm* — Venjuris P.C.

(57) ABSTRACT

A fixation system, which is developed for the treatment of diseases on a cervical, thoracal or lumbar spine and especially to maintain the distance between two vertebras on the spine and achieve fusion, is disclosed herein. The system preferably comprises a main cage (2), at least one dynamic shaft (3) fitted into the main cage (2) in parallel with cage axis, at least one sharp blade (5) fixed with a fixation pin (4) on to the shaft (3), and at least two imaging pins (6) located in two different axis-which helps to locate/identify the structure under X-Ray imaging during a surgery. A preferred sharp blade (5) is configured to turn 90° in the main cage (2) with the help of the shaft (3), and to penetrate into the vertebras with the help of sharp side surfaces (5.3) of the blade (5).

3 Claims, 7 Drawing Sheets

(52) U.S. Cl.
CPC ............... *A61F2002/30777* (2013.01); *A61F 2002/30779* (2013.01); *A61F 2002/30785* (2013.01); *A61F 2002/30845* (2013.01); *A61F 2002/30904* (2013.01); *A61F 2002/4475* (2013.01); *A61F 2310/00017* (2013.01); *A61F 2310/00023* (2013.01); *A61F 2310/00161* (2013.01); *A61F 2310/00179* (2013.01)

(56) References Cited

U.S. PATENT DOCUMENTS

| | | | |
|---|---|---|---|
| 6,572,619 B2 | 6/2003 | Santilli | |
| 6,770,096 B2* | 8/2004 | Bolger | A61B 17/0206 623/17.16 |
| 7,594,932 B2* | 9/2009 | Aferzon | A61F 2/447 623/17.16 |
| 7,867,277 B1 | 1/2011 | Tohmeh | |
| 8,100,972 B1* | 1/2012 | Bruffey | A61F 2/442 623/17.11 |
| 8,328,870 B2* | 12/2012 | Patel | A61F 2/4465 623/17.11 |
| 8,540,769 B2* | 9/2013 | Janowski | A61F 2/4455 623/17.11 |
| 8,545,562 B1* | 10/2013 | Materna | A61F 2/442 623/17.11 |
| 8,845,638 B2* | 9/2014 | Siegal | A61B 17/1671 606/170 |
| 9,107,760 B2* | 8/2015 | Walters | A61F 2/442 |
| 2002/0169507 A1 | 11/2002 | Malone | |
| 2002/0193880 A1 | 12/2002 | Fraser | |
| 2003/0149484 A1* | 8/2003 | Michelson | A61F 2/4455 623/17.16 |
| 2004/0172134 A1 | 9/2004 | Berry | |
| 2005/0283236 A1 | 12/2005 | Razian | |
| 2008/0027550 A1* | 1/2008 | Link | A61B 17/1671 623/17.16 |
| 2008/0215093 A1 | 9/2008 | Lin et al. | |
| 2008/0262623 A1 | 10/2008 | Bagga et al. | |
| 2009/0054987 A1 | 2/2009 | Chin et al. | |
| 2009/0099601 A1 | 4/2009 | Aferzon et al. | |
| 2009/0270990 A1 | 10/2009 | Louis et al. | |
| 2010/0249935 A1 | 9/2010 | Slivka et al. | |

FOREIGN PATENT DOCUMENTS

| | | |
|---|---|---|
| FR | 2930426 A1 | 10/2009 |
| FR | 2943529 A1 | 10/2010 |
| RU | 2251996 | 5/2005 |
| WO | 2010037926 A1 | 4/2010 |

* cited by examiner

FIXATION SYSTEM FOR SPINAL CAGES

TECHNICAL FIELD

The invention relates to a medical operation kit-to a fixation system for spinal cages in particular—which is developed in the treatment of diseases on cervical, thoracal and lumbar spine and especially to maintain the distance between two vertebras on the spine and achieve fusion.

STATE OF ART

Human spine is formed by connection of different-sized bone structures called vertebra. Spine is along the back and supports the body. The spine protects the spinal cord which is one of the most important parts of neural system, thus prevents damages to it. Although, the spine has a strong bone structure, it has an elasticity at the same time which enables adjustment to the body movements.

The cause of this elasticity is the intervertebral disks between vertebras. These disks are fibrous cartillage structures that are soft in the center and more solid in the outer parts. The main function of the disks is to give dynamic structure to the vertebra and to protect it against shocks.

One or couple of these disks can be damaged because of diseases, aging, accidents etc. In case of this, the movement capability of the vertebra can decrease. Additionally, the nerve roots passing through inside of the spine can be damaged or compressed. In such situation, at the organ that specific nerve is related to (i.e. arms or legs), a loss of strength and sensation or chronic back and/or lower back pains can be encountered. Many surgical techniques and methods were developed in the treatment of spinal vertebra diseases (fracture, kyphosis, degenerative disk disease, lordosis, spondylolisthesis).

Out of these techniques, the most commonly known is to remove the disk between vertebras and implant intervertebral devices (ALIF,TLIF,ACIF, PLIF) in place of it to maintain the distance between vertebras and speed up the fusion. The main purpose of these devices is to create the necessary medium for the ossification, to protect the distance between vertebra, to minimize the pressure on the nerves and to ensure non-deformation of the normal spinal curve until the fusion is achieved.

Since early 1900s, filling the place between two vertebra with another material technique is used in the treatment of intervertebral diseases. At the beginning, bone particles (autogenous-bone) taken from the patient's other bones (hip bone etc) were used for this purpose. Suitably-long bone part or parts taken from the patient himself/herself were placed between vertebras to treat the disease.

At the beginning of 1980s, stainless steel cages were invented by George Bagby. These cages were tested on animals first (especially on horses). Since 1989, cages manufactured from titanium alloy were used in clinical studies on humans. Using titanium cages were approved by American Food and Drug Administration (FDA) in 1996. Since then, several cages with different shapes (cylindrical, flat etc) and made of different materials (stainless steel, titanium alloy, PEEK-polyetheretherketone, ceramic, carbon alloy etc) were manufactured and in use for more than 15 years. The general characteristics of these cages are ; they should be in suitable size to fit the operated area, should have load-bearing walls and should have voids to enable application of bone material to speed up the fusion process.

Applications US20080262623 and US20020169507 are examples to the spinal cages. In general, this kind of cages were implanted between two adjacent vertebra with the help of an instrument suitable for the structure of the cage.

One of the problems arise from the use of cages is, migration and/or displacement of the cage because of the spinal movements after surgery. Due to this, to prevent the displacement of cage implanted between the vertebras, an extra plate and/or screw system can be used.

Application U.S. Pat. No. 6,572,619 is an example to plate systems used in spinal cages. These kind of plates can be used separately from the cage as it can be seen from Application US20090054987 or can be used combined with the cage as in Application US20080215093.

Apart from plates, another fixation method is to use additional screws suitable to the cage or blades combined with cages. As in the case of cages seen in Application US20020193880 and US 20100249935, the screws that passes through the cages or through the plates connected to the cages in crosswise and fixed to the upper and lower vertebras are used. After inserting the cage into the space between two vertebras, with the help of a suitable instrument, these screws were inserted into the bones and system is fixed. There are two circular blades, in the front part of the cage in Application U.S. Pat. No. 6,102,949. After placing the cage into its place, with the help of a suitable instrument, these circular blades, are stuck to the upper and lower bones by turning the blades and system fixation is achieved.

Fixation systems where plates and/or screws are used, bring along both the problem of extra implant usage and thus increase in costs, and the excessive damage to the vertebras. Because of the structure and the small sizes of the cervical vertebras increase the risk in such cases. Hence, a need to use a fixation system that will ensure non-migration of the cage after the surgery, that will give minimum damage to the upper and lower vertebra and that will be eliminate the use of extra plate and/or screw systems is arisen.

AIM OF THE INVENTION

The aim of the invention starting from the current status of the technique is: to achieve fusion in spine surgery operations and to eliminate the existing defects with the help of improvements made in cage systems that maintains the distance between two vertebras.

Another aim of this invention is to fix the intervertebral cages to the vertebras—with the help of a blade (or blades) which is placed in to the cage in parallel with the cage on a dynamic shaft- and is to prevent migration or displacement of the cage after the surgery. In this way, a more solid structure compared to the cage systems without a fixation element is achieved and to eliminate the use of an extra product i.e. plates to keep the cages within the vertebras and hence to minimize the damage to the vertebra tissue.

Another aim of the invention is the penetration of the blade into the vertebras without giving much damage to them due to special design of the sharp blade and fixing the system. In this way, operation time is shortened, the surgeon's safe operation possibility is much increased. Advantageously, during the operation the blade is positioned from horizontal position to vertical position and with the help of special tip design, it is stuck in to the vertebras with minimum damage and keeps it to be fixed until fusion is completed after the surgery. In this way, when the sharp blade is in open (vertical) position, the resistance of the system to vertebral movements and horizontal/vertical loads is increased. Advantageously during a revision surgery, this blade can be turned in the counter direction and brought back to the original position in the cage and cage can be pulled out between the vertebras.

Another aim of the invention is in cervical applications, the bottom of the main cage has a lordosis angled surface and due to this design, cage is solidly situated within the cervical spine. Advantageously, because of this characteristic, the natural form of the spine is maintained and less or over loading of lower and upper adjacent vertebra is prevented.

Another aim of the invention is, in addition to the imaging pins, during surgery under X-ray, the position of the cage within the vertebra can be identified easily as there is at least one metal dynamic shaft in parallel to the cage axis and at least one metal blade within the cage.

Another aim of the invention is that the part in the front of the cage is horizontally cut in the middle and thanks to the special design on the shaft, this horizontally cut cage structure can be expanded during fixation. Advantageously, after the system is implanted between the vertebras, the height of the system can be adjusted such that system height is closest to the distance between the vertebras with the help of expansion bumps on the tip of shaft. And the space between the vertebras is fully filled with the system. In this way, bottom and lower teeth and sharp blade on the main cage are firmly penetrated to the vertebras, hence the strength and function of the system is increased. Additionally, because of the special geometric structure of the shaft, blade fitting places on the cage, the number of blades regardless of the length and with of the cage, a very safe fixation is achieved.

DESCRIPTION OF FIGURES AND REFERENCE NUMBERS

In order to explain the invention better, drawings—which is detailed below—are attached:

FIG. 1. General overview of cage and fixation system
FIG. 2*a*. Top view of cage and fixation system
FIG. 2*b*. Top view of cage
FIG. 3. Back view of cage and fixation system
FIG. 4. Back view of cage and fixation system when the blade is in open position
FIG. 5. General overview of shaft and sharp blade fitted on it
FIG. 6. Side view of shaft
FIG. 7*a*. Side view of sharp blade
FIG. 7*b*. 3-D view of sharp blade
FIG. 8*a*. Top view of the system applied to PLIF cage
FIG. 8*b*. Side view of the system applied to PLIF cage
FIG. 8*c*. Back view of the system applied to PLIF cage
FIG. 9. Side cross-section of the system applied to Expandable Cage Parts of the FIGS. are numbered as follows:
1. Fixation system
2. Main cage
   2.1 Instrument fixation hole
   2.2 Shaft hole
   2.3 Instrument locking hole
   2.4 Top and bottom teeth
   2.5 Bone voids
   2.6 Angled front surface
   2.7 Sharp blade space
   2.8 Top and bottom surface
   2.9 Blade saddle
   2.10 Back surface
   2.11 Horizontal cut
   2.12 Cut-out lips
3. Shaft
   3.1 Hexagon back end
   3.2 Round front end
   3.3 Hexagon middle rise
   3.4 Fixation pin hole
   3.5 Expansion bumps
4. Fixation pin p1 5. Sharp blade
   5.1 Hexagon middle hole/rest
   5.2 Top and bottom arms
   5.3 Sharp side surfaces
   5.4 Movement-restraining side wall
   5.5 Sharp blade fixation pin hole
6. Imaging pin

DETAILED DESCRIPTION OF THE INVENTION

The fixation system for spinal cages comprises of in general terms; a main cage (2) placed between two vertebras, a dynamic shaft (3) placed in to the cage (2) in parallel with the cage (2) axis, at least one sharp blade (5) fixed on the shaft(3) with the help of a fixation pin (4) and minimum two imaging pins (6) which helps to identify the position of the structure under X-Ray during a surgery.

Figure 1:
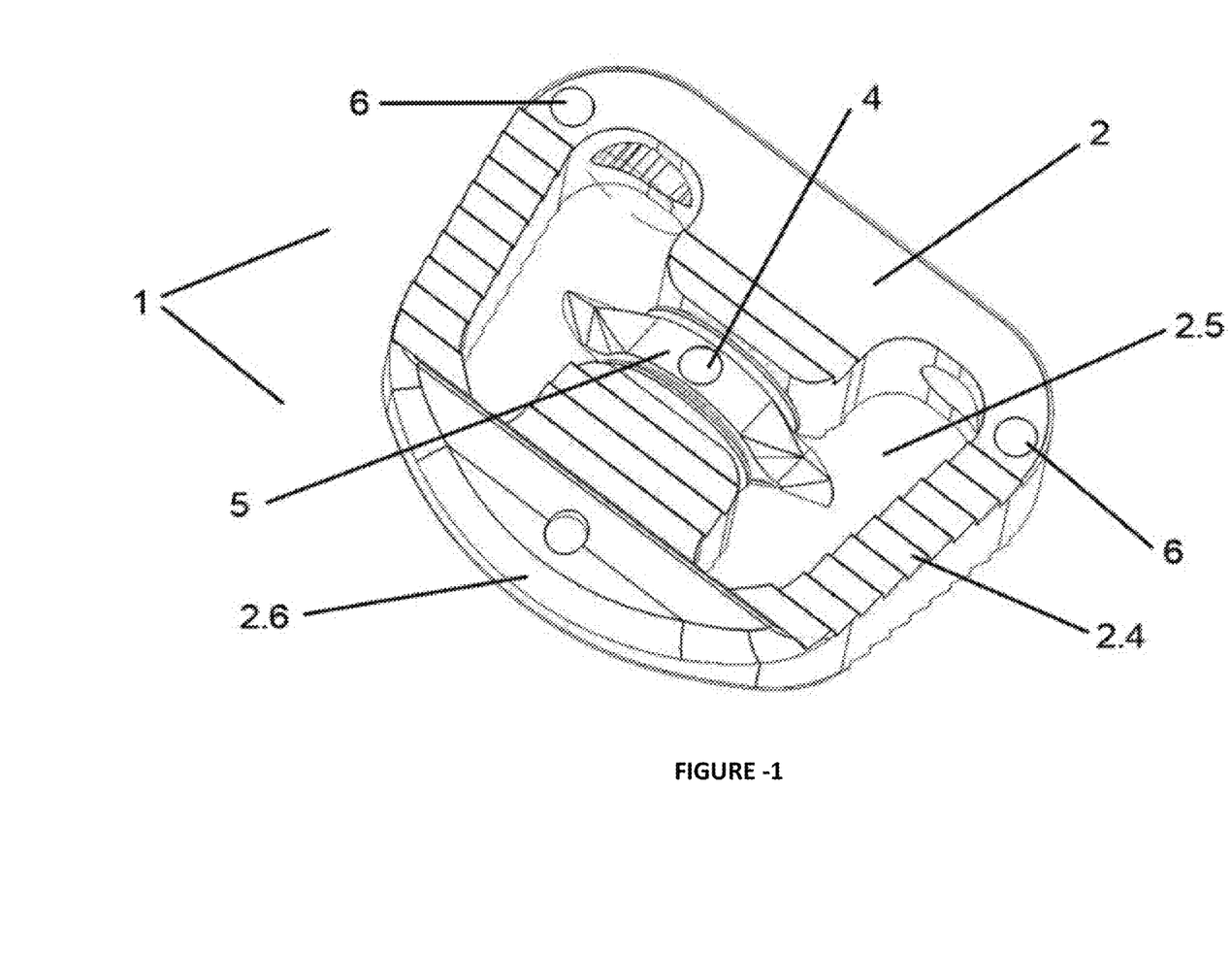
Figure 2:
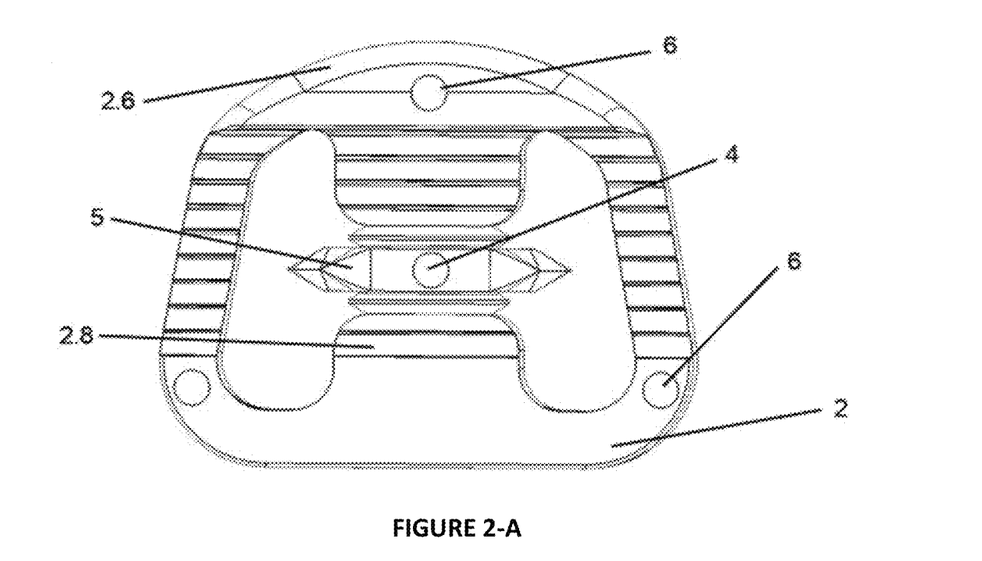
Figure 3:
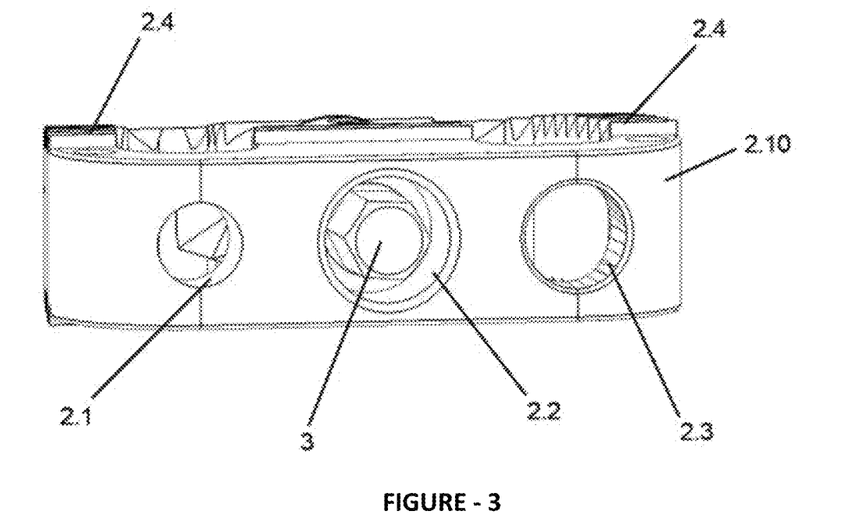

The main cage (2) shown in detail in FIG. 1-3 comprises of; an angled front surface (2.6) which helps the structure to be inserted between two vertebras, top and bottom teeth (2.4), top and bottom surface (2.8) back surface (2.10) with instrument fixation hole (2.1), shaft hole (2.2) and instrument fixation hole (2.3), bone voids (2.5), sharp blade space (2.7), imaging pin (6) and blade saddle (2.9).

Main cage (2) is preferable made of PEEK (polyetheretherketone) material. However it can be made of from stainless steel, titanium, titanium alloy, carbon, ceramic or a material that is bio compatible and strong enough to prevent damaging of the structure.

As an advantage, there are top and bottom teeth (2.4) that are in parallel to the horizontal axis of the main cage (2) on the top and bottom surfaces (2.8) of the main cage (2). These top and bottom teeth (2.4), helps keeping the main cage (2) after it has been implanted between two vertebra in position and preventing it to move backwards especially.

Back surface (2.10) consists of; a shaft hole (2.2) which will allow the entry of the tip of the instrument that will enable turning the shaft (3) and sharp blade (5), a suitable instrument locking hole (2.3) which is suitable to the tip of the instrument that will define the position of the system within two vertebras and will keep the system rigid and stable while it is being implanted between the two vertebras and preferably instrument fixation hole (2.1). Advantageously, these holes were positioned in a manner that will enable to use a single instrument which will carry out all these procedures. Instrument locking hole (2.3), may have a grooved structure or may have cavities which will allow the tips of the instrument to grasp it.

As an advantage, sharp blade space (2.7) is positioned at the center of main cage (2). In this way, a maximum space is obtained for the placement of sharp blade (5) and fusion—increasing bone materials that have been applied to bone voids (2.5) which are not affected much from the movements of sharp blade (5) during a surgery.

Figure 8A:
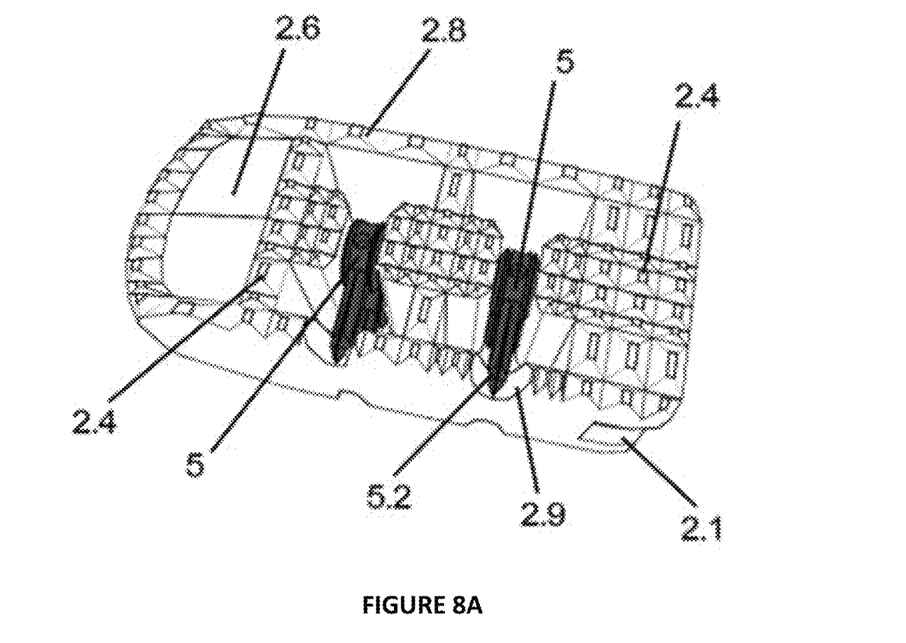
Figure 8B:
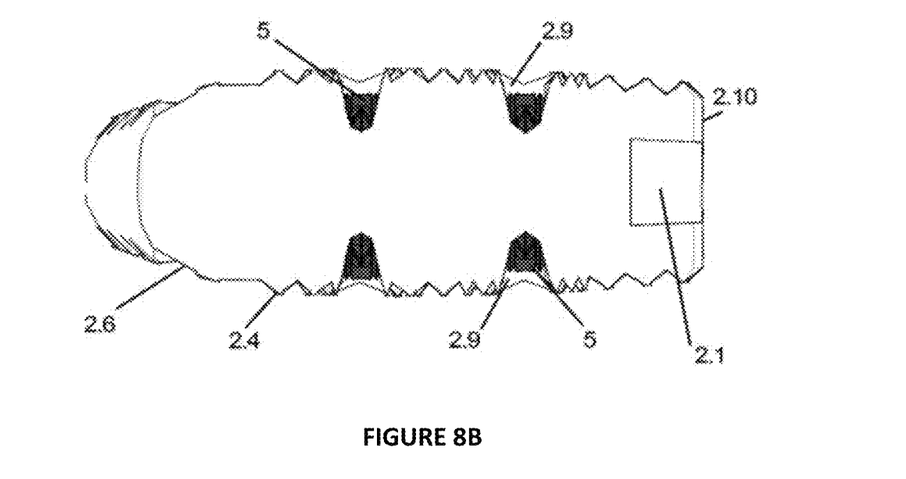

In another application of the invention, more than one shaft (3) are used and shafts (3) were placed such that they are closer to the cage surfaces rather than being at the center and in this way, blades (5) are allowed to do locking by going out of the cage. As seen in FIG. 8*a*, 8*b*, there are blade saddles (2.9) for the placement of top and bottom arms (5.2) of sharp blade (5) on the top and bottom surface (2.8) of main cage (2). When the sharp blade (5) is in closed position, top and bottom arms (5.2) rest on blade saddles (2.9). In this way, with the help of long top and bottom arms (5.2) of the sharp blade, it is ensured that the blades reach to the bone.

Figure 5:
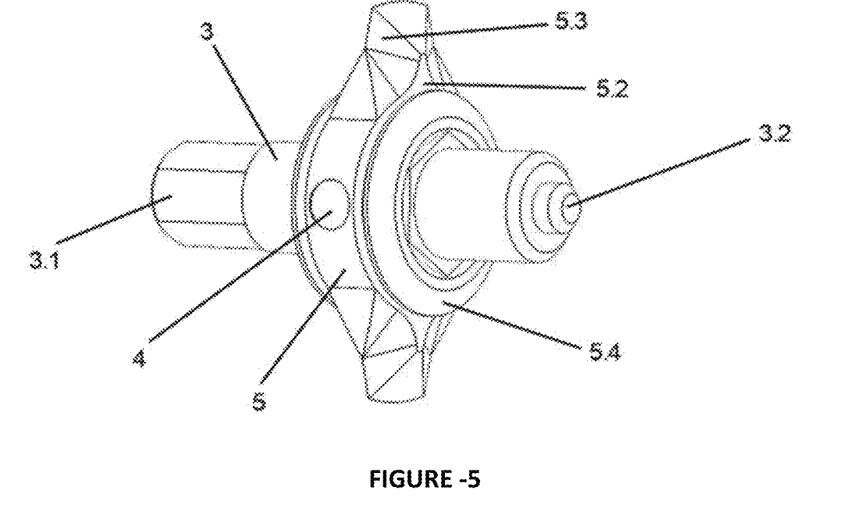
Figure 6:
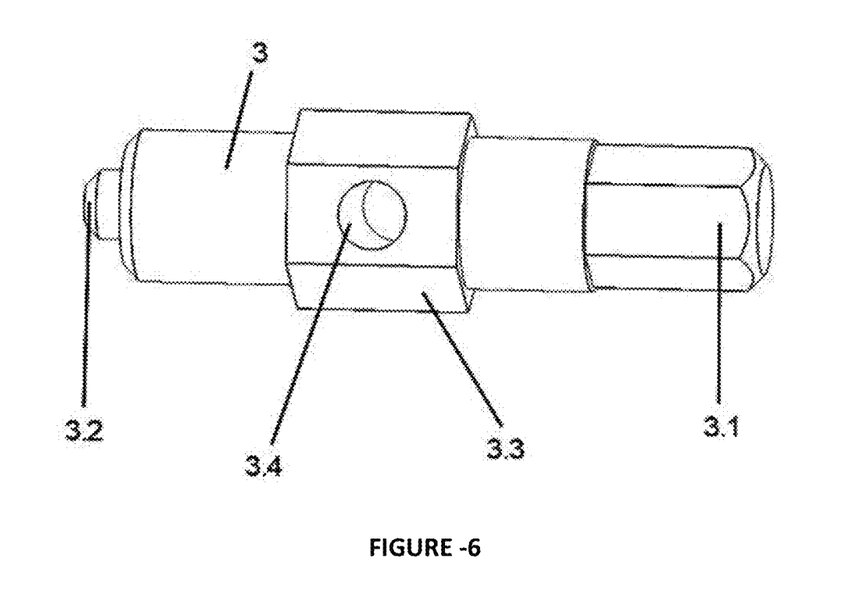

The shaft (3) seen in FIG. 5.6 in detail comprises of; hexagon back end (3.1), round front end (3.2), hexagonal middle rise (3.3), fixation pin hole (3.4) and preferably expansion bumps (3.5).

The shaft (3) is preferably preferable made of titanium alloy. However it can be made of from stainless steel, titanium, PEEK (polyetheretherketone), carbon, ceramic or a material that is bio compatible and strong enough to prevent damaging of the structure.

Advantageously, back end (3.1) of the shaft (3) has a hexagonal structure which enables a suitable instrument to grasp it and to turn the shaft (3) in the appropriate direction and angle. In this way, during a surgery the shaft (3) and the sharp blade (5) which is connected to it with a fixation pin (4), can be turned safely until the sharp blade (5) is penetrated into the vertebras in the appropriate position and fixation of the system is achieved. Round front end (3.2) of the shaft (3), has a round shape which will not prevent the movements of the shaft (3) within the main cage (2) and helps to define the position of the shaft (3) in the main cage (2).

As an advantage, the shaft (3) has a hexagonal middle rise (3.3) which helps the hexagonal middle hole (5.1) of the sharp blade (5) to rest on it. With the help of fixation pin hole (3.4) on the hexagonal middle rise (3.3), the sharp blade (5) is fixed on the shaft (3).

Figure 8C:
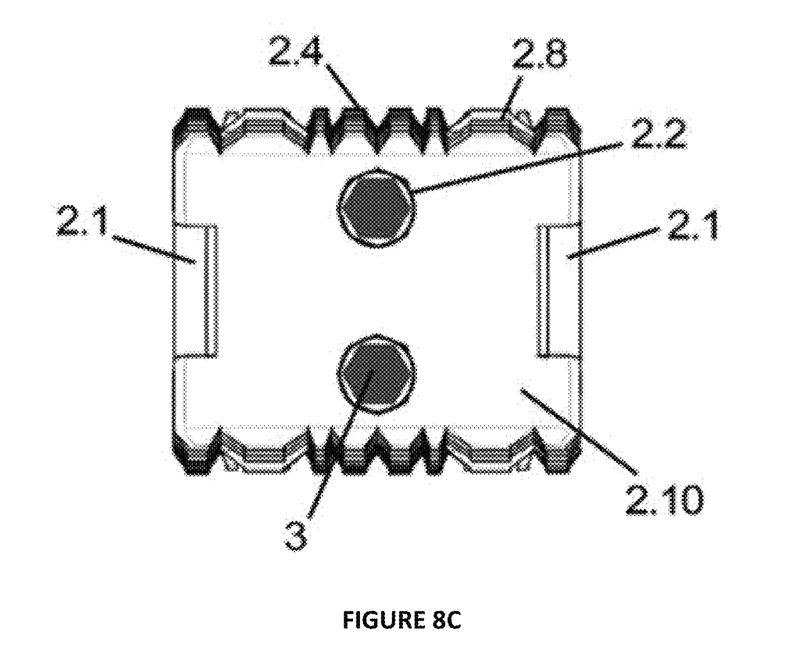

Advantageously, more than one shaft (3) can be fitted into the main cage (2) (FIG. 8a, 8b, 8c). In this case, the shafts (3) can be positioned side by side, on top of each other or diagonally in the main cage (2). In such a case, there will be more than one shaft hole (2.2) on the back surface (2.10) of main cage (2).

Figure 7A:
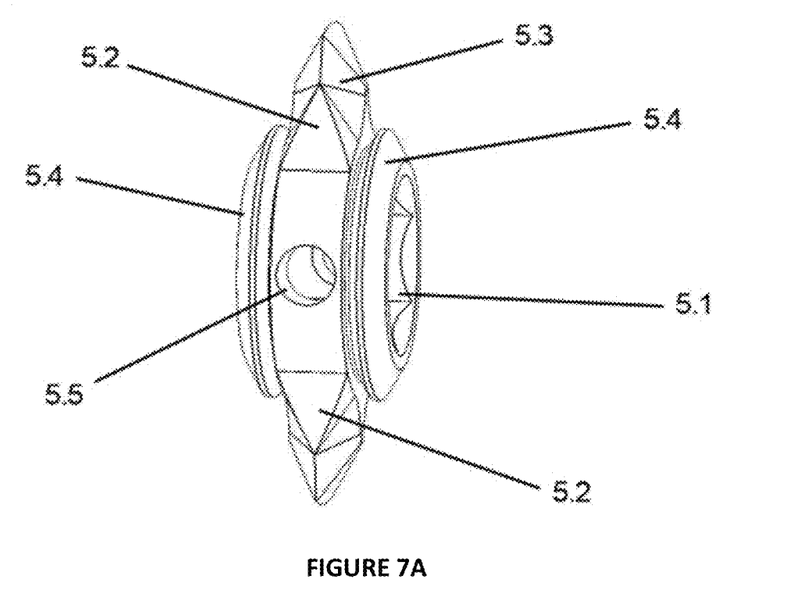
Figure 7B:
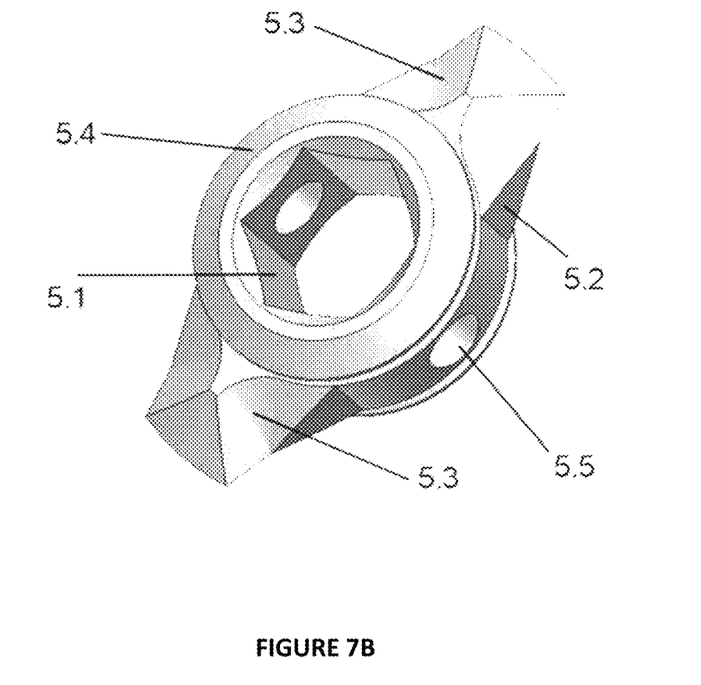

The sharp blade (5) seen in FIG. 7 in detail comprises of; hexagonal middle rest (5.1), top and bottom arms (5.2), sharp side surfaces (5.3), movement restraining side walls (5.4) and sharp blade fixation pin hole (5.5).

The sharp blade (5) is preferably made of titanium alloy. However it can be made of from stainless steel, titanium, PEEK (polyetheretherketone), carbon, ceramic or a material that is bio compatible and strong enough to prevent damaging of the structure.

The sharp blade (5) is placed into the sharp blade space (2.7) on the main cage (2). Advantageously, the sharp blade (5) is tightly fitted into the sharp blade space (2.7) with the help of movement-restraining side walls (5.4) that are on both sides of sharp blade (5) and in this way, free and uncontrolled movements of sharp blade (5) is prevented.

The sharp blade (5) is placed on the hexagonal middle rise (3.3) on the shaft (3) with the help of hexagonal middle hole/rest (5.1) and it is fixed to the shaft (3) with the help of fixation pin (4) that passes through sharp blade fixation pin hole (5.5). In this way, sharp blade (5) moves in parallel with the movements of the shaft (3).

The sharp side surfaces (5.3) that are on the top and bottom arms (5.2) of the sharp blade (5) has a concave triangular shape. In this way, the sharp side surfaces (5.3) easily penetrate to the bone when inserted into the vertebras and they ensure the fixation of the system without much damaging the bones.

The sharp blade (5), at initial position within the main cage (2), is on horizontal axis and in parallel position to the main cage (2). In the final position, the sharp blade (5)—which is turned by a suitable instrument and thus turned by the shaft (3) and penetrated to the vertebras—is in 90° vertical position to the main cage (2) in the horizontal axis.

As an advantage, there can be more than one sharp blade (5) within the fixation system (1). In such a case, either there are at least two sharp blades (5) in sequence on the same shaft (3) or there are at least two sharp blades (5) in sequence on at least two different shafts (3). These sharp blades (5) can have one top and one bottom arm (5.2) as well as they can have either top and/or bottom arm. In case the structure of main cage (2) is not suitable to fully accommodate the sharp blades (5), there can be blade saddles (2.9) on the top and bottom surface (2.8) of the main cage (2) into which the top and bottom arms (5.2) of the sharp blades (5) can rest (FIG. 8). One or couple of these possibilities can be utilized depending on the geometric structure of the main cage (2) and the area of usage.

Advantageously, there are at least two imaging pins (6) on the main cage (2) in horizontal and/or vertical position. These imaging pins (6) help to identify the position of the structure under X-ray imaging during the surgery. The surgeon can easily identify the correct position of the cage (2) as the pins (6) are located at the back side of the cage(2) and the blade (5) is seen under X-Ray.

Figure 9:
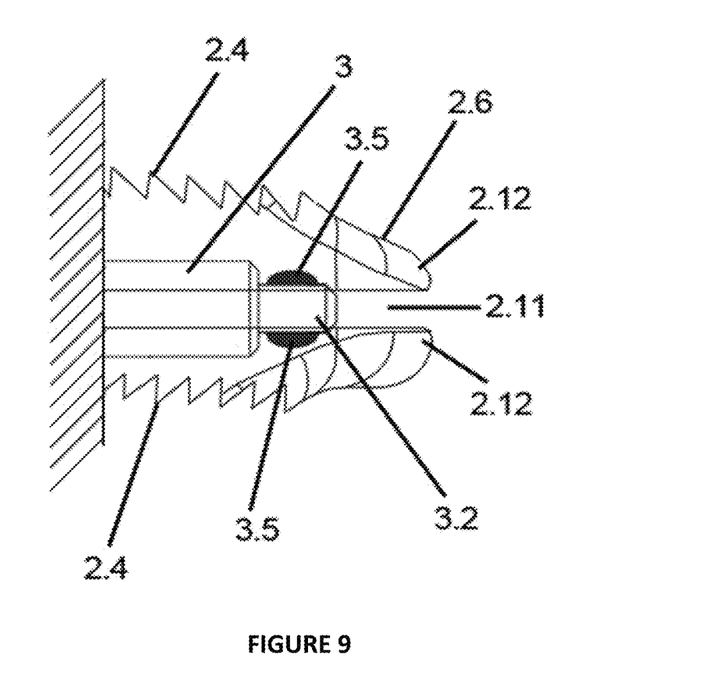

As an advantage, fixation system (1) can be applied to the expandable cage systems. In such a case, the angled front surface (2.6) of the main cage (2) is cut into two by a horizontal cut (2.11) and there are two expansion bumps (3.5) on round front end (3.2) of the shaft (3). Depending on the movement of the shaft (3), these expansion bumps (3.5) opens the horizontal cut (2.11) by pushing the cut-out lips (2.12) on angled front surface (2.6) of the main cage (2) downwards and upwards and changes the height of the main cage (2) can be adjusted appropriately to the distance between the vertebras.

In a sample application of the invention;

The distance between the vertebras in the part to be operated is properly measured and appropriate size of the main cage (2) is decided. Proper main cage (2), with the help of instrument fixation hole (2.1) and instrument locking hole (2.3) on the back surface (2.10), is locked to the suitable instrument. Then, with the same instrument, it is inserted into the place between two vertebras. During this process, one should pay attention to the possibility of placing the main cage (2) into too deep as to give damage to the spine and into the very front which may lead to the displacement of it after the surgery. After the main cage (2) is inserted into its place, another part of the same instrument is fixed to the hexagonal back end (3.1) of the shaft (3). By turning the shaft (3) and the sharp blade (5) that is fixed on it in the proper direction and angle, the top and bottom arms (5.2) of the sharp blade (5) is penetrated to the top and bottom vertebras.

Figure 4:
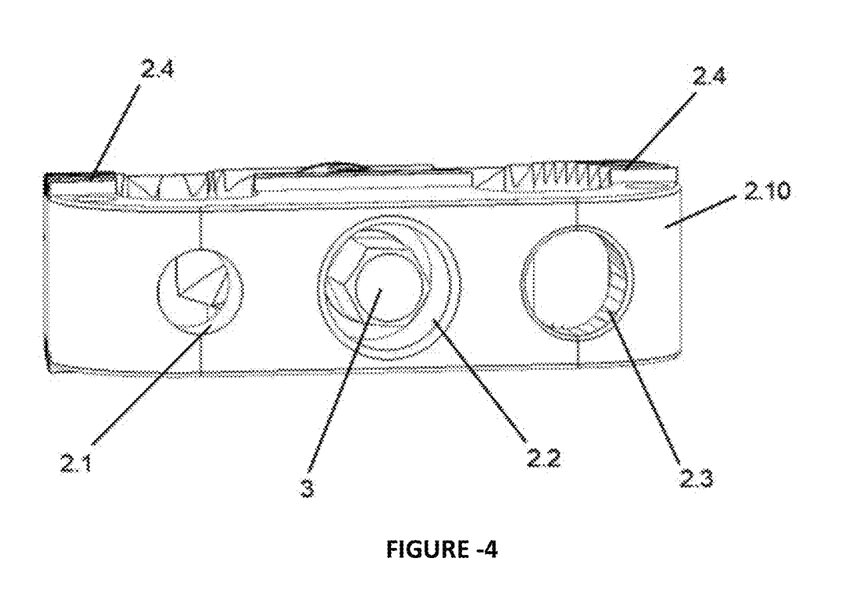

After controlling the position and angle of the sharp blade (5) preferably with an imaging method and making sure that position is correct, the instrument is pulled out from the main cage (2) and fixation system (1) is fitted into its place. FIG. 4 shows the final position of the system. Hence, depending on the movements of the spine, until the fusion is completed, it is ensured that the system stays fixed in its place and no need is arised to use an extra screw and/or plate for fixation.

The invention is described by way of example above. Of course, the invention cannot be limited with the above described applications and the person skilled in the art can implement various variants of the invention without going beyond the ambit of the patent.

The invention claimed is:

1. A fixation system (1) for maintaining a distance between two vertebras on a patient's spine at a fixation stage of a surgery, the fixation system (1) comprising:
    a main cage (2) having a sharp blade space (2.7),
    at least one dynamic shaft (3) fitted into the main cage (2), the shaft having a hexagonal middle rise (3.3), and at least one sharp blade (5) fixed on to the shaft (3) and located at the sharp blade space (2.7), the sharp blade(5) having:
- a. a top and a bottom arms (5.2) configured to penetrate into the vertebras bi-directionally during the fixation stage, each of the arms (5.2) comprising a plurality of triangular concave sharp side surfaces (5.3) and cutting edges each formed by at least two of the triangular concave sharp side surfaces (5.3) and configured to allow the arms (5.2) to penetrate into the vertebras bi-directionally;
- b. a hexagonal middle rest (5.1) configured to rest on the hexagonal middle rise (3.3) of the shaft (3); and
- c. movement-restraining side walls (5.4) configured to restrict a blade movement within the sharp blade space (2.7).

2. A fixation system according to claim 1, wherein the main cage (2) further comprises an angled front surface (2.6) with a horizontal cut (2.11) and two cut-out lips (2.12) separated by the horizontal cut (2.11); and the shaft (3) further comprises a round front end (3.2) and at least one expansion bump (3.5) located at the round front end (3.2), the expansion bump (3.5) being configured to expand and further separate the cut-out lips during the fixation stage.

3. A fixation system (1) for maintaining a distance between two vertebras on a patient's spine at a fixation stage of a surgery, the fixation system (1) comprising:

a main cage (2) with:
- a. a top and a bottom surfaces (2.8),
- b. a back surface (2.10),
- c. an instrument fixation hole (2.1) located at the back surface (2.10),
- d. a shaft hole (2.2) located at the back surface (2.10),
- e. an instrument locking hole (2.3) located at the back surface (2.10),
- f. top and bottom teeth (2.4) located at the top and bottom surfaces (2.8),
- g. an angled front surface (2.6),
- h. bone voids (2.5) located between the angled front surface (2.6) and the back surface (2.10),
- i. a sharp blade space (2.7) located between the bone voids (2.5),
- j. a horizontal cut (2.11) located at the angled front surface (2.6), and
- k. cut out lips (2.12) located at the angled front surface (2.6) and separated by the horizontal cut (2.11);

one dynamic shaft (3)—placed in the main cage (2)—with:
- a. a hexagon back end (3.1),
- b. a round front end (3.2),
- c. a hexagon middle rise (3.3),
- d. a fixation pin hole (3.4) located at the hexagon middle rise (3.3), and
- e. expansion bumps (3.5) located at the round front end (3.2);

a fixation pin (4) configured to mate with the fixation pin hole (3.4); and at least one sharp blade (5) fixed on the shaft (3) by the fixation pin (4), the blade (5) comprising:
- a. a hexagon middle hole/rest (5.1) configured to rest on the middle rise (3.3),
- b. a top and a bottom arms (5.2) extending away from the middle hole/rest (5.1),
- c. triangular concave side surfaces (5.3) located at the top and the bottom arms (5.2),
- d. cutting edges, each formed by at least two of the triangular concave side surfaces (5.3) and configured for the top and the bottom arms (5.2) to penetrate into the vertebras bi-directionally during the fixation stage,
- e. a movement-restraining side wall (5.4) located at an end of the blade (5), and
- f. a sharp blade fixation pin hole (5.5) configured to receive the fixation pin (4) to fix the blade (5) on the shaft (3), wherein when the shaft (3) moves during the fixation stage, the blade (5) penetrates into the vertebras, and the expansion bumps (3.5) simultaneously expand and further separate the cut-out lips (2.12).

\* \* \* \* \*